United States Patent [19]
Merritt et al.

[11] Patent Number: 5,560,544
[45] Date of Patent: Oct. 1, 1996

[54] ANTI-CLOGGING ATOMIZER NOZZLE

[75] Inventors: Joyce R. Merritt, Fairfield; Mark T. Lund, West Chester, both of Ohio

[73] Assignee: The Procter & Gamble Company, Cincinnati, Ohio

[21] Appl. No.: 265,311

[22] Filed: Jul. 1, 1994

[51] Int. Cl.$^6$ .................................................. B05B 1/28
[52] U.S. Cl. ........................................ 239/104; 239/492
[58] Field of Search .................................... 239/337, 492, 239/104, DIG. 22, 491, 461; 222/148

[56] References Cited

U.S. PATENT DOCUMENTS

| | | | |
|---|---|---|---|
| 2,371,557 | 3/1945 | Sullivan | 220/31 |
| 2,557,048 | 6/1951 | Haase | 220/31 |
| 3,231,150 | 1/1966 | Holm et al. | 222/355 |
| 3,254,677 | 6/1966 | Wakeman | 137/630.22 |
| 3,378,205 | 4/1968 | Barker | 239/337 |
| 3,570,770 | 3/1971 | Ewald | 239/337 |
| 3,584,789 | 6/1971 | Traynor | 239/117 |
| 3,587,942 | 6/1971 | Gailitis | 222/402.24 |
| 3,785,571 | 1/1974 | Hoening | 239/337 |
| 4,055,305 | 10/1977 | Schwinn | 239/524 |
| 4,392,503 | 7/1983 | Watanabe | 132/83 R |
| 4,422,086 | 12/1983 | Miura et al. | 346/140 R |
| 4,513,877 | 4/1985 | Taguchi et al. | 220/335 |
| 4,555,062 | 11/1985 | You | 239/690 |
| 4,583,690 | 4/1986 | You | 239/690 |
| 4,623,906 | 11/1986 | Chandrashekhar et al. | 346/140 R |
| 4,643,948 | 2/1987 | Diaz et al. | 428/422 |
| 4,728,392 | 3/1988 | Miura et al. | 156/644 |
| 4,751,532 | 6/1988 | Fujimura et al. | 346/140 R |
| 4,801,955 | 1/1989 | Miura et al. | 346/140 R |
| 4,941,614 | 7/1990 | Ilott | 239/294 |
| 5,105,988 | 4/1992 | Knickerbocker | 222/148 |
| 5,105,998 | 4/1992 | Knickerbocker | 222/148 |
| 5,119,116 | 6/1992 | Yu | 346/140 R |
| 5,119,991 | 6/1992 | Divers | 239/117 |
| 5,196,064 | 3/1993 | Branderhorst et al. | 118/313 |
| 5,207,785 | 5/1993 | Knickerbocker | 222/148 |
| 5,219,076 | 6/1993 | Crosby et al. | 209/210 |
| 5,267,693 | 12/1993 | Dickey | 239/417.3 |
| 5,358,149 | 10/1994 | O'Neill | 222/321 |

FOREIGN PATENT DOCUMENTS

| | | |
|---|---|---|
| 0506128A1 | 9/1992 | European Pat. Off. . |
| 1306254 | 9/1962 | France . |
| 2689100 | 6/1992 | France . |
| 2644321 | 4/1978 | Germany . |
| 2709796 | 9/1978 | Germany . |
| 3827512 | 2/1990 | Germany . |
| 1586170 | 3/1981 | United Kingdom . |
| 2088748 | 6/1982 | United Kingdom . |
| 2140392 | 11/1984 | United Kingdom . |
| 2200617 | 8/1988 | United Kingdom . |

*Primary Examiner*—Kevin Weldon
*Attorney, Agent, or Firm*—Daniel F. Nesbitt; Michael E. Hilton; William Scott Andes

[57] ABSTRACT

The present invention provides an improved atomization system for dispensing and atomizing a fluid product having film-forming characteristics. The atomization system includes a nozzle for atomizing the fluid product which has been formed of a reduced wettability composition including a base material and a wettability-reducing component for reducing the wettability of the base material with the fluid product. The reduced-wettability attribute ensures that the product will tend to "bead up" on the surfaces of the nozzle assembly rather than wetting or coating the surfaces. The surfaces will thus tend to repel the product, once the supply pressure driving the fluid toward the nozzle is relieved, leaving the critical nozzle surfaces substantially free of a film of product which would tend to dry and form a residue on the critical nozzle surfaces when exposed to atmospheric air. The reduced wettability of the nozzle assembly is preferably achieved through the addition of a melt additive to impart the desired characteristics to the nozzle base material. Improved atomizer nozzles according to the present invention also preferably incorporate a change in cross-sectional area of the nozzle passages to further enhance the migration of the fluid away from the nozzle orifice once the supply pressure is relieved utilizing capillary pressure phenomena.

18 Claims, 3 Drawing Sheets

ANTI-CLOGGING ATOMIZER NOZZLE

FIELD OF THE INVENTION

The present invention relates to atomization systems useful for dispensing and atomizing various fluid products in conjunction with a source of pressurized fluid. More particularly, the present invention relates to improved atomization systems which provide for reduced clogging of a nozzle assembly following use.

BACKGROUND OF THE INVENTION

Many fluid products are utilized by atomizing them into a mist consisting of a multitude of fine fluid droplets. This atomization process is frequently accomplished by providing a source of pressurized fluid and a nozzle through which the pressurized fluid is directed. The source of pressurized fluid can be provided, for example, by a manually actuated pump or by a pressurized container wherein the pressurization may be provided by a propellant which is soluble in the fluid, an atmospheric gas, or other form of pressurization. Upon exiting from the nozzle through one or more orifices, the fluid stream is broken apart into many small, airborne droplets. The fluid product may then be utilized in the form of an airborne cloud or fog, or more commonly the fluid product in atomized form is directed toward a surface to be coated with the product.

Atomizer nozzles may take many forms, including, for example, pressure-swirl nozzles which expel the product in an expanding, swirling hollow cone of fluid which breaks up or shears into fine fluid particles, impingement-type nozzles which impinge two or more streams of product to disintegrate the fluid into fine particles, and other types as well.

Many fluid products exhibit a tendency to solidify or dry out when exposed to atmospheric air, leaving behind a film or layer of dried product on any surface which was initially wetted with product in liquid form. While this may be a desirable characteristic on certain receiving surfaces, such a dried film or layer typically has a negative impact when the surface is the interior of a fluid passage or a nozzle orifice. A dried film or layer of product on the walls of a passage or the sides of a nozzle orifice will tend to narrow the passage or orifice, particularly as the build-up increases over time. Such a buildup often results in an uneven, roughened surface which tends to increase the rate of build-up.

Atomizer nozzles are particularly susceptible to build-up of dried product, as the nozzle passages and orifices are comparatively small and have dimensions which are critical to producing the desired spray pattern. As the surfaces of the nozzle passages and orifices become coated with dried product accumulated between dispensing operations, the spray pattern produced typically becomes more irregular and has larger and more unevenly-sized fluid particles. The fluid may emerge in large droplets, or even a solid stream of un-atomized liquid product. Eventually, if the build-up is severe enough, fluid flow through the nozzle may become completely obstructed, and the nozzle will cease to function.

Over the years, many attempts have been made to address the clogging of atomizer nozzles. Most rely upon mechanical means, such as moveable pins, sleeves, or scrapers to either seal the nozzle from the atmosphere (thus preventing drying of un-dispensed product) or to mechanically clear dried product from the nozzle orifice(s) or passages.

Such devices require additional parts, frequently moveable, which adds to the complexity and cost of the resulting nozzle, as well as poor aesthetic qualities. Particularly in today's era of mass-production, molded plastic parts, additional elements which must be separately molded and assembled are of particular concern.

Accordingly, it would be desirable to provide an atomizer nozzle which would exhibit a reduced tendency to clog with dried product residue, yet be economical to produce and reliable in service.

SUMMARY OF THE INVENTION

The present invention provides an improved atomization system for dispensing and atomizing a fluid product having film-forming characteristics. The atomization system includes a nozzle for atomizing the fluid product which has been formed of a reduced wettability composition including a base material and a wettability-reducing component for reducing the wettability of the base material with the fluid product.

The reduced wettability attribute ensures that the product will tend to "bead up" on the surfaces of the nozzle rather than wetting or coating the surfaces. The surfaces will thus tend to repel the product, once the supply pressure driving the fluid toward the nozzle is relieved, leaving the critical nozzle surfaces substantially free of a film of product which would tend to dry and form a residue on such surfaces when exposed to atmospheric air.

Improved atomizer nozzles according to the present invention also preferably incorporate a change in cross-sectional area of the nozzle passages to further enhance the migration of the fluid away from the nozzle orifice once the supply pressure is relieved. The change in cross-sectional area utilizes capillary pressure phenomena to move fluid away from the nozzle passages and nozzle orifice, thus enhancing the fluid-repellency of the nozzle assembly by eliminating continuous fluid contact with the nozzle surfaces once the dispensing operation is completed.

The resulting nozzle provides improved anti-clogging performance without the addition of separate, moveable mechanical elements. The simplicity of the nozzle equates to a very user-friendly atomization system which is cost effective to produce and reliable in operation.

BRIEF DESCRIPTION OF THE DRAWINGS

The present invention will be better understood with reference to the following Detailed Description and to the accompanying Drawing Figures, in which:

FIG. 1 is an elevational sectional view of an atomizer assembly according to an embodiment of the present invention.

FIG. 2 is an elevational, partially sectional view of the nozzle insert depicted in FIG. 1 taken along line 2—2.

FIG. 3 is a diagrammatical illustration of the definition and measurement of contact angles according to the present invention.

FIG. 4 is a diagrammatical illustration of a fluid passageway according to the present invention in an initial condition.

FIG. 5 is a diagrammatical illustration of the fluid passageway of FIG. 4 in a final condition.

FIG. 6 is an elevational sectional view of an atomizer assembly according to another embodiment of the present invention.

FIG. 7 is an elevational sectional view of an atomizer assembly according to a further embodiment of the present invention.

Unless otherwise indicated, like elements are identified by like numerals throughout the Drawing Figures.

DETAILED DESCRIPTION OF THE INVENTION

Figures 1, 2:
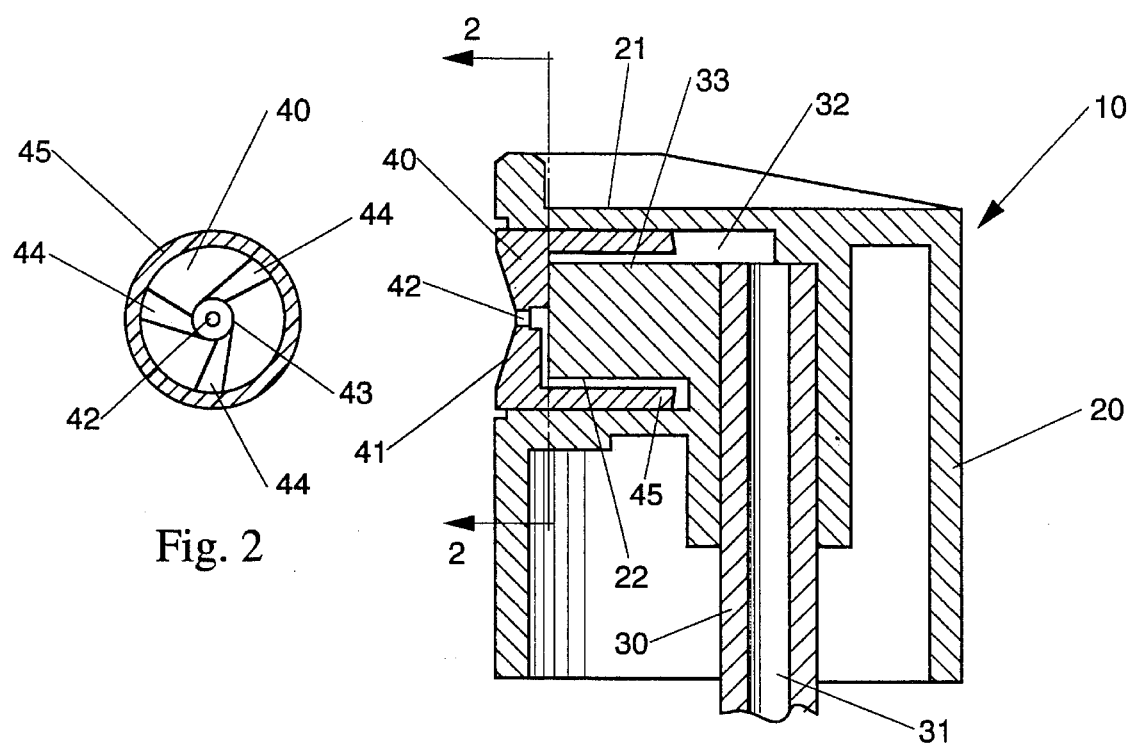

FIG. 1 depicts an atomizer assembly 10 according a preferred embodiment of the present invention. The atomizer assembly 10 preferably includes an actuator housing 20, a stem 30, and a nozzle insert 40. The atomizer assembly 10 is preferably secured via stem 30 to either a manually actuated pump mechanism or an aerosol valve which is fitted to a suitable container (not shown) for containing the fluid product prior to dispensing.

In the preferred atomizer assembly depicted in FIG. 1, the nozzle insert 40 is of the pressure swirl type. Pressure swirl atomizers are quite common in the industry and are commonly used to atomize such products as hair sprays, hard surface cleaners, pretreaters, perfumes, throat sprays, spray starch, and automotive products. One of the most common types of swirl atomizers includes a single outlet orifice and is provided in the form of an insert for inclusion in an atomizer assembly to permit the insert 40 to be molded separately from the actuator housing 20. As more clearly seen in FIG. 2, which is a cross-sectional view of the nozzle insert 40, typical elements of a nozzle insert 40 of the pressure swirl variety include a nozzle face 41, an outlet orifice 42, a swirl chamber 43, a plurality of radial swirl vanes 44, and an outer wall 45 which secures the insert in the actuator housing 20. Other variations of the swirl atomizer design would include a nozzle insert having an uninterrupted inner surface with the swirl vanes being molded into the post itself.

The stem 30 is in fluid communication with a container which contains the product and a suitable source of fluid under pressure. The stem defines a supply passage 31 for the pressurized fluid to conduct it into the interior of the actuator housing 20. Once inside the actuator housing 20, the fluid passes into an annular supply passage 32 which is bounded on the outside by a wall 21 and on the inside by a post 22.

The nozzle insert 40, in a typical atomizer assembly, fits securely in the cavity bounded by wall 21 and is inserted to its optimum position relative to post 22 and locks into place. The nozzle insert 40 and wall 21 typically have a mating ring and groove pair (not shown) to accomplish securement of the insert. This securement is important because movement of the insert into and out of the cavity changes the dimensions of the fluid passageways behind the insert and may have a significant effect on the performance of the atomizer assembly. Outer wall 45 is in fluid-tight contact with the wall 21, such that all pressurized fluid is directed into the annular feed channel 33 between the inner surface of outer wall 45 and the surface of the post 22. The feed channel 33 conducts the pressurized fluid into the outer ends of the swirl vanes 44 depicted in FIG. 2.

When the atomizer assembly is actuated, the fluid travels up through the stem 30 and into the actuator housing 20. The fluid then travels though feed channel 33 located between the outer wall 45 and the post 22, and into swirl vanes 44 which impart rotational energy to the fluid in the swirl chamber 43. The rotating fluid then exits the outlet orifice 42 in a thin-walled, expanding, rotating conical film. The thin film is broken when instabilities cause the fluid to break up into ligaments and droplets to form a spray.

In atomizer assemblies of the type herein described, the swirl vanes 44 (three are typically used) and outlet orifice 42 are among the smallest passageways in the entire assembly. Such small passages and orifices tend to be more susceptible to clogging and obstruction than larger passageways such as the feed channel 33, which in the particular atomizer depicted has an annular form.

The dimensions of the nozzle passages and orifices are critical to producing the desired spray pattern. As the surfaces of the nozzle passages and orifices become coated with dried product accumulated between dispensing operations, the spray pattern produced typically becomes more irregular and has larger and more unevenly-sized fluid particles. Irregular sprays typically occur when one of the swirl vanes become partially blocked, creating an uneven flow in the swirl chamber. The fluid may emerge in large droplets, or even a solid stream of un-atomized liquid product. Eventually, if the build-up is severe enough, fluid flow through the nozzle may become completely obstructed, and the nozzle will cease to function.

In order to address this shortcoming in currently available nozzle assemblies, the present invention provides an improved nozzle insert which is formed of a material which exhibits a reduced wettability versus currently commercially available nozzle materials. Reduced wettability reduces the likelihood of clogging by rendering the surfaces of the fluid passages in the nozzle insert fluid-repellent, at least to a degree.

Figure 3:
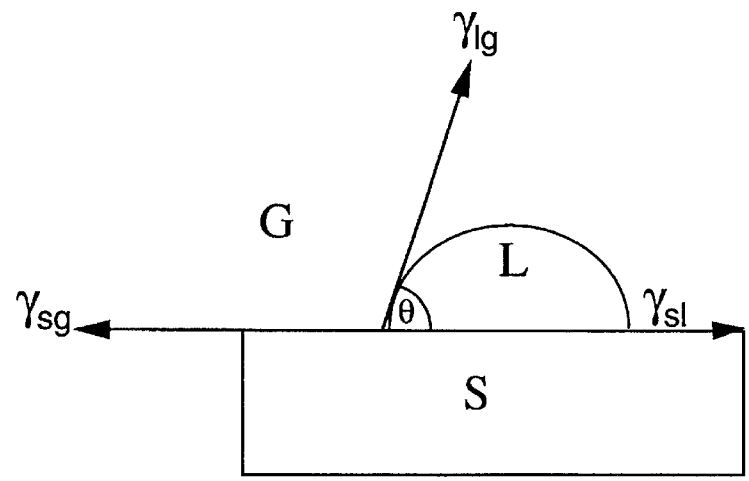
Figure 4:
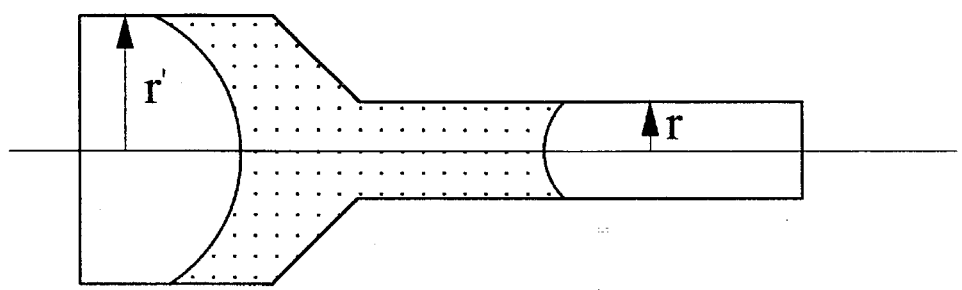
Figure 5:
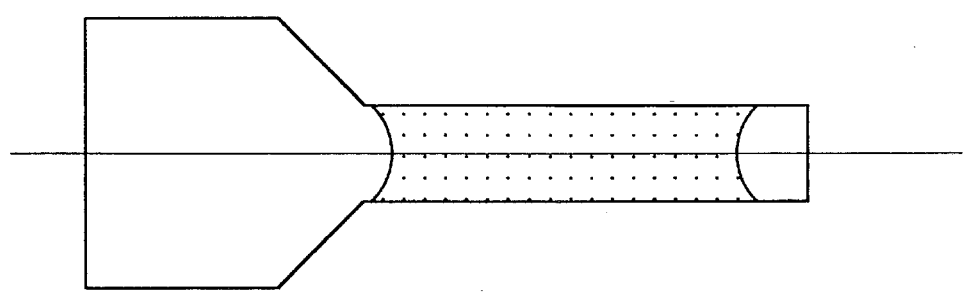

FIG. 3 is a schematic illustrating the parameters and definitions critical to determining wettability of a solid surface, which can be quantified in terms of a contact angle. FIG. 3 illustrates a droplet of liquid L that is surrounded by a gas G and resting on a solid surface S having a contact angle of Θ. Note that for perfect wetting of the solid surface with the liquid, the contact angle would be 0 degrees, and for perfect non-wetting the contact angle would be 180 degrees. The three surface tension forces are those between the solid and gas $\gamma_{sg}$), the liquid and the gas $\gamma_{lg}$), and the solid and the liquid $\gamma_{sl}$). Balancing these three forces in the horizontal direction for the equilibrium condition results in equation (1):

$$\gamma_{sg}=\gamma_{sl}+\gamma_{lg}\cos\Theta \quad (1)$$

Solving equation (1) for cos Θ yields equation (2):

$$\cos\Theta=(\gamma_{sg}-\gamma_{sl})/\gamma_{lg} \quad (2)$$

To maximize repellency, the contact angle Θ is maximized. As can be seen from equation (2), the lower the surface tension between the liquid and the gas, the more difficult it is to obtain high contact angles resulting in repellency. For example, it is much easier to repel water ($\gamma_{lg}$=72 dynes/cm) than alcohol ($\gamma_{lg}$=23 dynes/cm). Once $\gamma_{lg}$ is fixed, the contact angle is maximized by using a material that reduces $Y_{sg}$ (sometimes referred to as critical surface tension) as much as possible. In the present invention, dried product films are prevented from forming on the critical inner surfaces of the nozzle insert and the nozzle orifice. This is accomplished by using a material or surface treatment that tends to repel the fluid to be atomized. For a more detailed discussion of equation (1), known as Young's equation, see Young, T., Trans. Roy. Soc. (London), 95, 65 (1805).

Materials of interest in the present invention for fabrication of the reducedwettability nozzle inserts can be characterized by the contact angles they produce with particular fluids. For example, currently available nozzle materials will provide a given contact angle with a particular product. The beneficial aspects of utilizing the wettability-reducing nozzle materials of the present invention may be quantitatively measured in terms of the absolute or relative change in the contact angle as compared with that of the standard nozzle material with the same fluid product.

Compared with conventional nozzle materials, the reduced wettability nozzle materials of the present invention preferably provide at least about a 20% increase in contact angle, more preferably at least about a 40% increase in contact angle, and under some circumstances with certain products may provide more than a 300% increase in the contact angle. In absolute terms, the resulting contact angle is preferably at least about 35 degrees, more preferably at least about 40 degrees, with the objective being to maximize the contact angle within the limits of economic and practical constraints.

It should be noted that surfaces with low wettability do not necessarily have a low coefficient of friction, and vice versa. As such, materials and/or coatings which may be desirable from the standpoint of reducing surface tension of a fluid product may not produce a low coefficient of friction. Materials and/or coatings which, on the other hand, produce a low coefficient of friction may not exhibit low wettability characteristics.

Indeed, the roughness of a surface has been found to be a factor when attempting to maximize the contact angle of a fluid, and hence maximize repellency. The following equation (3), derived by Wenzel, illustrates this phenomenon:

$$\cos \Theta = (\gamma_{sg} - \gamma_{sl})/\gamma_{lg} xr \qquad (3)$$

where $r = a/A = da/dA \geq 1$ a = actual area of interface

A = "apparent" area of the "geometrical" interface

Because of the sign change of $\cos \Theta$ at $\Theta = 90$ degrees, for $\Theta < 90$ degrees roughness decreases the contact angle, and for $\Theta > 90$ degrees roughness increases the contact angle. Roughness effects thus depend upon the properties of the fluid. A more detailed discussion of this phenomenon may be found in R. N. Wenzel, Ind. Eng. Chem., 28, 988 (1936), and R. N. Wenzel, J. Phys. Colloid Chem., 53, 1466 (1949).

In operation, an atomization system according to the present invention is utilized to dispense and atomize the requisite quantity of fluid product, or in the case of a manually actuated pump mechanism, a pumping stroke is completed during the dispensing process. Once the supply pressure is relieved, several factors tend to produce a small amount of empty space within the passages leading to the nozzle orifice. In mechanically actuated pumps, for example, the momentum of the fluid at the moment the pumping stroke is stopped causes a small quantity of fluid to exit the orifice after the supply of fluid from the pump mechanism has been interrupted. In addition to this factor, in aerosol-type dispensing configurations a small mount of solubilized propellant will continue to boil off from the fluid product in the region of the orifice, increasing the concentration of and reducing the volume of the product remaining within the passages leading to the nozzle orifice.

During the following period of non-use and/or between dispensing cycles, the fluid-repelling properties of the nozzle insert then come into play, repelling the fluid away from the nozzle orifice and nozzle passages (particularly the swirl vanes) and back through the internal passages such that the empty space is adjacent to the nozzle. This leaves the nozzle orifice and the critical passageways adjacent to the nozzle orifice substantially free of fluid, such that these surfaces which are exposed to atmospheric air during non-use are substantially free of a film of product which would tend to dry and form a residue on such surfaces. In this fashion, the features of the present invention substantially reduce if not eliminate the difficulties in nozzle clogging present in the prior art.

Fluid migration in atomization systems according to the present invention is also believed to be enhanced by the presence of passage surfaces upstream of the reduced-wettability nozzle assembly which have a greater wettability than the nozzle assembly, and which thus tend to attract fluid from surfaces having a lower degree of wettability.

An additional feature which is presently preferred for inclusion in nozzle assemblies according to the present invention further enhances the migration of the fluid away from the nozzle orifice once the supply pressure is relieved. Nozzle assemblies according to the present invention preferably incorporate a change in the cross-sectional area of the feed passage 33 to utilize capillary pressure phenomena to move fluid away from the nozzle passages and nozzle orifice and ensure that the empty space contained within the fluid passages is adjacent to the nozzle assembly. This enhances the fluid-repellency of the nozzle insert by eliminating continuous fluid contact with the regions of the nozzle containing the orifice and the critical internal passages leading to the orifice. By eliminating such continuous fluid contact and aiding in the fluid migration away from the nozzle itself, as the nozzle surfaces repel the fluid product via their reduced wettability characteristics there is clear space for the repelled fluid to move into and away from the nozzle itself.

FIGS. 4 and 5 schematically illustrate this phenomenon. FIG. 4 depicts a fluid passage having two different cross-sectional areas and a quantity of fluid remaining in the passage such as at the moment of cessation of fluid flow. For fluid/surface combinations producing a contact angle of less than 90 degrees, the net driving pressure forces the fluid from the passage region of larger radius denoted as r' into the region of smaller radius denoted as r. The net driving pressure is defined in equation (4):

$$Pcap=2\gamma\cos \Theta(1/r-1/r') \quad (4)$$

where Pcap=capillary driving pressure

γ=surface tension

Θ=contact angle r, r'=radius of passage at respective locations (=½ of hydraulic diameter for non-cylindrical passages)

For fluid/surface combinations producing a contact angle of greater than 90 degrees, the principles illustrated in FIGS. 4 and 5 would be reversed, i.e., the fluid would tend to move from the region of smaller radius r toward the region of larger radius r'.

Using this same principle, a nozzle assembly can be designed to force the product away from the critical geometry of the nozzle insert. FIGS. 6 and 7 illustrate designs that tend to move fluid via capillary action away from the nozzle insert 40. FIGS. 6 and 7 depict a change C in cross-sectional area of the annular feed channel 33 via a difference in the outer diameter of the channel which is formed by the inner surface of the outer wall 45. Note that the change C depicted in FIGS. 6 and 7 has been exaggerated for clarity, and due to manufacturing considerations and fluid characteristics it may be less pronounced. FIG. 7 is configured according to FIGS. 4 and 5, i.e., wherein the contact angle is less than 90 degrees, while FIG. 6 is configured for the situation wherein the contact angle would be greater than 90 degrees. The change in diameter may be accomplished by, for example, forming an undercut in the mold producing the inner surface of the outer wall 45.

Figure 6:
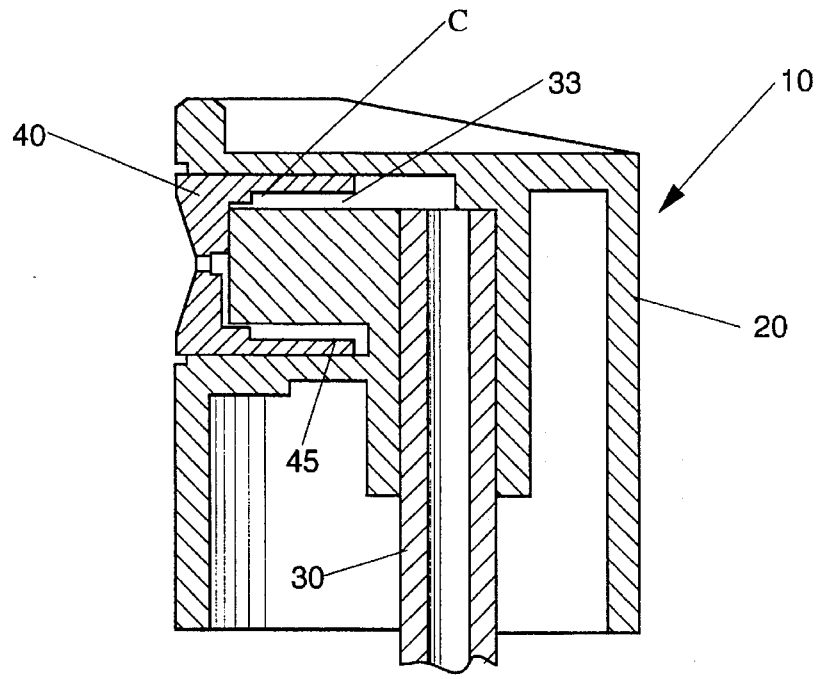
Figure 7:
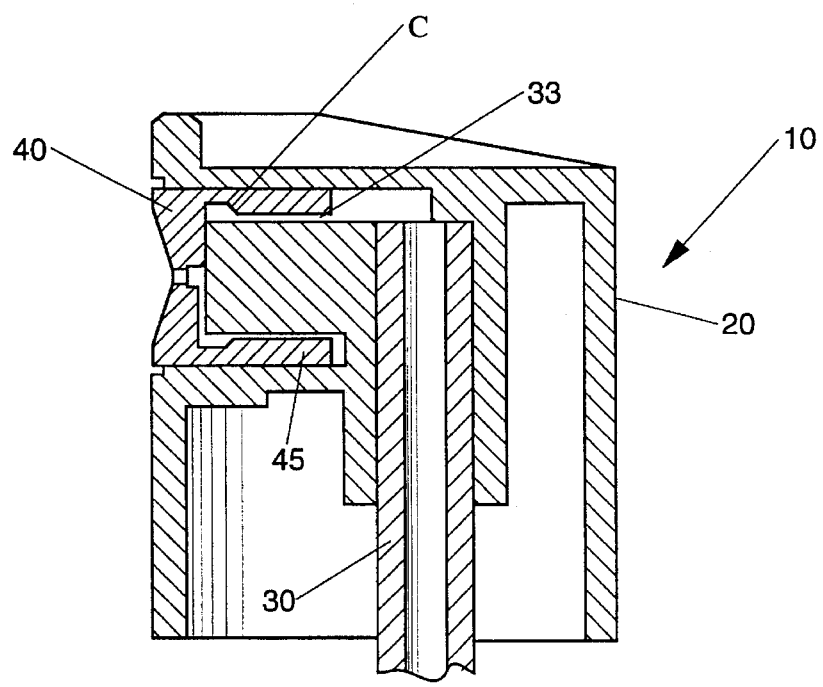

The change in cross-sectional area may be a sharp change, such as depicted in FIG. 6, or a more gradual transition such as depicted in FIG. 7, particularly when necessitated by manufacturing considerations. The cross-sectional area may be varied by a change in the inner or outer diameter of an annular passage, such as depicted in FIGS. 6 and 7, or a variation in width or depth of a rectangular passage, or the diameter of a cylindrical passage, for example.

In operation, once again an atomization system according to the present invention is utilized to dispense and atomize the requisite quantity of fluid product, or in the case of a manually actuated pump mechanism, a pumping stroke is completed during the dispensing process. Once the supply pressure is relieved, several factors tend to produce a small amount of empty space within the passages leading to the nozzle orifice. In mechanically actuated pumps, for example, the momentum of the fluid at the moment the pumping stroke is stopped causes a small quantity of fluid to exit the orifice after the supply of fluid from the pump mechanism has been interrupted. In addition to this factor, in aerosol-type dispensing configurations a small amount of solubilized propellant will continue to boil off from the fluid product in the region of the orifice, increasing the concentration of and reducing the volume of the product remaining within the passages leading to the nozzle orifice.

During the following period of non-use and/or between dispensing cycles, the capillary function of the change in the cross-sectional area of the internal fluid passages moves fluid away from the nozzle region. The fluid-repelling properties of the nozzle insert then come into play, repelling the fluid away from the nozzle orifice and nozzle passages (particularly the swirl vanes) and back through the internal passages into the space vacated by the fluid retreating under the capillary action such that the empty space is adjacent to the nozzle. This leaves the nozzle orifice and the critical passageways adjacent to the nozzle orifice substantially free of fluid, such that these surfaces which are exposed to atmospheric air during non-use have no remaining product to form a film or layer of dried product residue. In this fashion, the features of the present invention substantially reduce if not eliminate the difficulties in nozzle clogging present in the prior art.

Fluid migration in atomization systems according to the present invention is also believed to be enhanced by the presence of passage surfaces upstream of the reduced-wettability nozzle assembly which have a greater wettability than the nozzle assembly, and which thus tend to attract fluid from surfaces having a lower degree of wettability.

The nozzle insert itself may be manufactured via any known conventional method. Injection molding of the insert is a presently preferred method of economically manufacturing the nozzle inserts useful in the present invention. The advantages of the present invention in terms of controlling the wettability of the nozzle insert may be obtained through the use of a melt additive which is incorporated into the primary or base material of the nozzle insert. An alternative approach to the use of a melt additive would be to apply a suitable coating to the nozzle insert after formation of the nozzle insert itself.

Any commercially available materials may be used as the primary nozzle insert material, as well as the other components of the atomization system. Such materials include plastic materials such as polypropylene and polyoxymethylene (POM), which is commercially available under the name acetal. For its generally favorable mold release properties, low cycle time, hardness, and dimensional stability, acetal is currently preferred as a primary nozzle insert material.

For the presently preferred configuration wherein the nozzle insert is to be injection molded from a plastic resin material such as acetal, the preferred method of controlling the wettability of the nozzle insert is to incorporate a melt additive into the resin. Such melt additives may include, for example, silicone, polytetrafluoroethylene (PTFE), available under the trade name TEFLON ® from DuPont, or other fluorochemicals. Silicone is presently preferred for use with the preferred acetal resin material. The concentration of the melt additive to be utilized is highly dependent upon the characteristics of the base nozzle insert material and the properties of the fluid product, and also depends upon the geometry of the particular nozzle configuration in that, for example, the surface finish of the nozzle material may impact the contact angle as discussed above, passages of smaller cross-sectional area tend to exhibit greater capillarity with a given product than larger passages, etc.

For product formulations in general, it is desirable to obtain a contact angle of at least about 40 degrees, and preferably higher, to develop sufficiently reduced wettability characteristics to obtain the advantages of the present invention. In terms of utilizing a melt additive to reduce the wettability of the material, concentrations of the melt additive are preferably between about 0.1 wt. % and about 50 wt. % (such that the additive remains a minor component of the material), more preferably between about 0.5 wt. % and about 20 wt. %, still more preferably between about 1 wt. % and about 5 wt. %, and for the particular materials presently preferred, about 2 wt. %.

The benefit of a given concentration of melt additive wettability control material is preferably maximized through the use of what is known as "blooming" of the additive material to the surface of the molded nozzle insert. This phenomenon occurs when the melt additive material at the time of molding is homogeneously dispersed throughout the nozzle insert, but after molding tends to migrate toward the surface of the insert such that a concentration gradient is achieved with a greater concentration at the surface and a lesser concentration near the center. Blooming continues until an equilibrium condition is reached with a particular concentration gradient dependent upon the composition of the molded material. With a nozzle insert molded of a silicone/acetal resin, for example, the silicone molecules tend to have a greater attraction for each other than for the acetal. As such, they tend to orient themselves toward the surface of the molded part and then toward each other.

Blooming may be accelerated through exposure to elevated temperatures after the nozzle inserts are molded, but frequently satisfactory results may be obtained by simply maintaining the inserts at typical room temperatures for a given period of time. The "blooming time" will of course depend upon such factors as the nozzle base material, the melt additive material, and the desired concentration gradient.

An alternative approach is to form the nozzle insert in conventional fashion with conventional materials and to apply a suitable surface coating to the surfaces of the nozzle insert. Suitable coating materials include those mentioned above in the melt additives context, namely silicone, TEFLON ®, and other fluorochemicals, as well as other materials such as waxes and long chain fatty acids.

The improved atomizer nozzles of the present invention may be utilized to atomize a wide variety of fluid products, being particularly advantageous with those fluid products having film-forming characteristics (i.e., that tend to form a film or layer of dried product residue when they evaporate). Examples of such products include hair sprays, hard surface cleaners, pretreaters, perfumes, throat sprays, spray starch, and automotive products. One particular product of current interest is in the area of hair styling compositions.

Contact angles referred to herein are based upon experimental measurements taken with a Model 100-00 Goniometer manufactured by Rame-Hart, Inc. using conventional methodology. The use of other appropriate instrumentation and experimental methods may provide equally acceptable results in measuring the contact angles of fluids on particular surfaces.

Although the Drawing Figures depict pressure swirl atomizers for use in the present invention, it is to be understood that the principles of the present invention may be applied to other nozzle geometries as well, including impingement type nozzles and hybrid nozzles incorporating both swirl chambers and impinging fluid streams, for example. Dispensing and atomization systems incorporating multiple nozzles and/or atomizer assemblies of a single configuration or differing configurations may incorporate the principles of the present invention.

The source of pressurized fluid conducted to the nozzle assembly may take many forms, such as pressurized aerosol-type containers (such as those wherein the pressurization is provided by a propellant which is soluble in the fluid), continuously pressurized/supplied systems which incorporate some sort of bulk supply with a driven pump system, and manually actuated pump mechanisms. The present invention is believed to be particularly advantageous for use with atomization systems which are intermittently actuated, and thus experience frequent periods of non-use which cause many opportunities for product films to build up in nozzle orifices and internal passages.

In addition, while much of the foregoing discussion has focused on the scenario in which the functional nozzle geometry is contained in a nozzle "insert", it would be apparent to one of ordinary skill in the art that the advantages of the present invention may be applied to other configurations as well, such as where the nozzle is integrally molded as part of the actuator or is part of another structural member. Other variations in nozzle geometry may includes versions in which all or part of the interior passageways are formed as part of another component, such as the post depicted in the Drawing Figures, behind the nozzle insert itself.

To further enhance the performance of atomizer assemblies according to the present invention, in the instances where a nozzle insert only forms one side of or a portion of a passageway, it may be desirable to reduce the wettability of the mating part (i.e., actuator housing, etc.) as well, such that all sides of a passageway have similar wettability properties.

While particular embodiments of the present invention have been illustrated and described, it would be obvious to those skilled in the art that various changes and modifications can be made without departing from the spirit and scope of the present invention. For example, the product composition, the size and shape of the overall dispenser, the size and shape of the application/distribution surface, the dimensions, ratios, clearances, and tolerances of the nozzle components, the manufacturing methods, the materials utilized, and their concentrations may all be tailored to suit particular applications. It is intended to cover in the appended claims all such modifications that are within the scope of this invention.

EXAMPLE

An exemplary embodiment of a nozzle insert having reduced wettability according to the present invention was prepared for the following hair styling composition (all percentages by weight): 4% Silicone Grafted Polymer (comprising 60% t-butyl acrylate/20% acrylic acid/20% silicone macromer (weight average molecular weight of silicone macroruer of about 10,000), having a weight average molecular weight of about 150,000), 3% Isododecane (PERMETHYL 99A, from Presperse, Inc., South Plainfield, N.J., USA), 0.20% Acetyl triethyl citrate (CITROFLEX A-2, from Mofflex, Inc., Greensboro, N.C., USA), 0.40% Potassium hydroxide, 0.10% Perfume, 16% Water, and 75.3% Ethanol (SDA 40 (100% ethanol)). This product was prepared by first preparing a polymer premix with the ethanol, neutralizing the polymer with the potassium hydroxide (added as a 45% aqueous solution), then adding sequentially with mixing, water, isododecane, plasticizer, and perfume.

According to this exemplary embodiment, a nozzle insert having the configuration depicted in FIGS. 1 and 2 for use in an atomizer assembly having a manually actuated pump mechanism was molded from a reduced wettability material comprising about 98 wt. % acetal and about 2 wt. % silicone as a melt additive. The nozzle inserts had three swift vanes having a rectangular cross-sections and dimensions of 0.010" wide and 0.015" deep. The outlet orifice 42 had a diameter of 0.013". The nozzle insert was molded utilizing conventional injection molding techniques, methods, and conditions. A "plaque" (circular disk) of this material was similarly molded for contact angle measurements with the above-described product, and the contact angle measured was 46 degrees, whereas a plaque of 100% acetat resin (the current industry standard for nozzle materials) only provided a contact angle of 32 degrees. The resulting increase in the contact angle was about 44%.

The nozzle insert was subjected to a blooming time of 1 week at ambient temperatures, which had been found to produce satisfactory results with the particular hair styling composition herein described. This nozzle insert configuration when molded from the reduced wettability material described exhibited reduced clogging tendencies when compared to acetal nozzle inserts of the same configuration.

What is claimed is:

1. An atomization system for dispensing and atomizing a fluid product having film-forming characteristics, said atomization system including a nozzle for atomizing said fluid product, said nozzle having an orifice and an internal fluid passage leading to said orifice, said nozzle being formed of a reduced wettability composition, said reduced wettability composition comprising a base material and a wettability-reducing component, said wettability-reducing component comprises a melt additive intermixed with said base material for reducing the wettability of said base material with said fluid product such that when a dispensing operation is concluded said orifice and said internal fluid passage substantially repel said fluid product to prevent film formation on and clogging of said nozzle.

2. The atomization system of claim 1, wherein said melt additive comprises from about 0.1 wt. % to about 50 wt. % of said reduced wettability composition.

3. The atomization system of claim 1, wherein said melt additive comprises about 2 wt. % of said reduced wettability composition.

4. The atomization system of claim 1, wherein said wettability-reducing component comprises silicone.

5. The atomization system of claim 1, wherein said wettability-reducing component comprises a fluorochemicals.

6. The atomization system of claim 1, wherein said base material comprises polyoxymethylene.

7. The atomization system of claim 1, wherein said atomization system includes an intermittent source of said fluid product.

8. The atomization system of claim 1, wherein said reduced wettability composition produces a contact angle of at least about 40° with said fluid product.

9. The atomization system of claim 1, wherein said internal fluid passage comprises a swirl vane leading to said orifice.

10. The atomization system of claim 1, wherein said nozzle comprises a nozzle insert having a surface and a center, and wherein said melt additive has a greater concentration at said surface and a lesser concentration at said center.

11. The atomization system of claim 10, wherein said melt additive is dispersed in a concentration gradient.

12. The atomization system of claim 1, wherein said atomization system includes an actuator assembly, and wherein said nozzle comprises a nozzle insert which is inserted into an opening in said actuator assembly.

13. The atomization system of claim 12, wherein said nozzle comprises a pressure swirl atomizer nozzle.

14. The atomization system of claim 1, wherein said internal fluid passage includes a change in cross-sectional area within said nozzle such that capillary action upon said fluid product in said internal fluid passage draws said fluid product in a direction away from said orifice when said dispensing operation is concluded to prevent film formation on and clogging of said nozzle.

15. An atomization system for dispensing and atomizing a fluid product having film-forming characteristics, said atomization system including a nozzle for atomizing said fluid product, said nozzle having an orifice and an internal fluid passage leading to said orifice, said nozzle being formed of a reduced wettability composition, said reduced wettability composition comprising a base material and a wettability-reducing component for reducing the wettability of said base material with said fluid product such that when a dispensing operation is concluded said orifice and said internal fluid passage substantially repel said fluid product to prevent film formation on and clogging of said nozzle, wherein said atomization system includes an actuator assembly, and wherein said nozzle comprises a nozzle insert which is inserted into an opening in said actuator assembly, and wherein said nozzle comprises a pressure swirl atomizer nozzle.

16. The atomization system of claim 15, wherein said wettability-reducing component comprises silicone.

17. The atomization system of claim 15, wherein said wettability-reducing component comprises a fluorochemical.

18. An atomization system for dispensing and atomizing a fluid product having film-forming characteristics, said atomization system including a nozzle for atomizing said fluid product, said nozzle having an orifice and an internal fluid passage leading to said orifice, said nozzle being formed of a reduced wettability composition, said reduced wettability composition comprising a base material and a wettability-reducing component for reducing the wettability of said base material with said fluid product, said fluid product having a contact angle $\Theta$ when resting on said reduced wettability composition, when a dispensing operation is concluded said orifice and said internal fluid passage substantially repel said fluid product to prevent film formation on and clogging of said nozzle, said internal fluid passage includes a change in cross-sectional area within said nozzle such that said internal fluid passage has a region of larger cross-sectional area and a region of smaller cross-sectional area, when said contact angle $\Theta$ is less than 90° said fluid product tends to move from said region of larger cross-sectional area toward said region of smaller cross-sectional area, and when said contact angle $\Theta$ is greater than 90° said fluid product tends to move from said region of smaller cross-sectional area toward said region of larger cross-sectional area, this capillary action upon said fluid product in said internal fluid passage draws said fluid product in a direction away from said orifice when said dispensing operation is concluded to prevent film formation on and clogging of said nozzle.

\* \* \* \* \*